US00PP30024P3

(12) United States Plant Patent
Biancheri

(10) Patent No.: US PP30,024 P3
(45) Date of Patent: Dec. 25, 2018

(54) ***RANUNCULUS ASIATICUS* PLANT NAMED 'ABIZANAGI'**

(50) Latin Name: *Ranunculus asiaticus*
Varietal Denomination: ABIZANAGI

(71) Applicant: Alberto Biancheri, Camporosso Mare (IT)

(72) Inventor: Alberto Biancheri, Camporosso Mare (IT)

(73) Assignee: Impresa Individuale Biancheri Alberto (IT)

( * ) Notice: Subject to any disclaimer, the term of this patent is extended or adjusted under 35 U.S.C. 154(b) by 0 days.

(21) Appl. No.: 15/731,507

(22) Filed: Jun. 20, 2017

(65) Prior Publication Data

US 2018/0020585 P1 Jan. 18, 2018

(30) Foreign Application Priority Data

Jul. 13, 2016 (QZ) ..... PBR 2016/1773

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
See application file for complete search history.

*Primary Examiner* — Anne Marie Grunberg
(74) *Attorney, Agent, or Firm* — Cassandra Bright

(57) ABSTRACT

A new and distinct *Ranunculus* cultivar plant named 'ABIZANAGI' is disclosed, characterized by deep magenta colored flowers. Plants are highly productive and consistently produce quality flowers through the season. Flower stems are above average in length. The new variety is a *Ranunculus*, normally produced as a cut flower and also potentially useful as an ornamental plant.

2 Drawing Sheets

Figure 1:
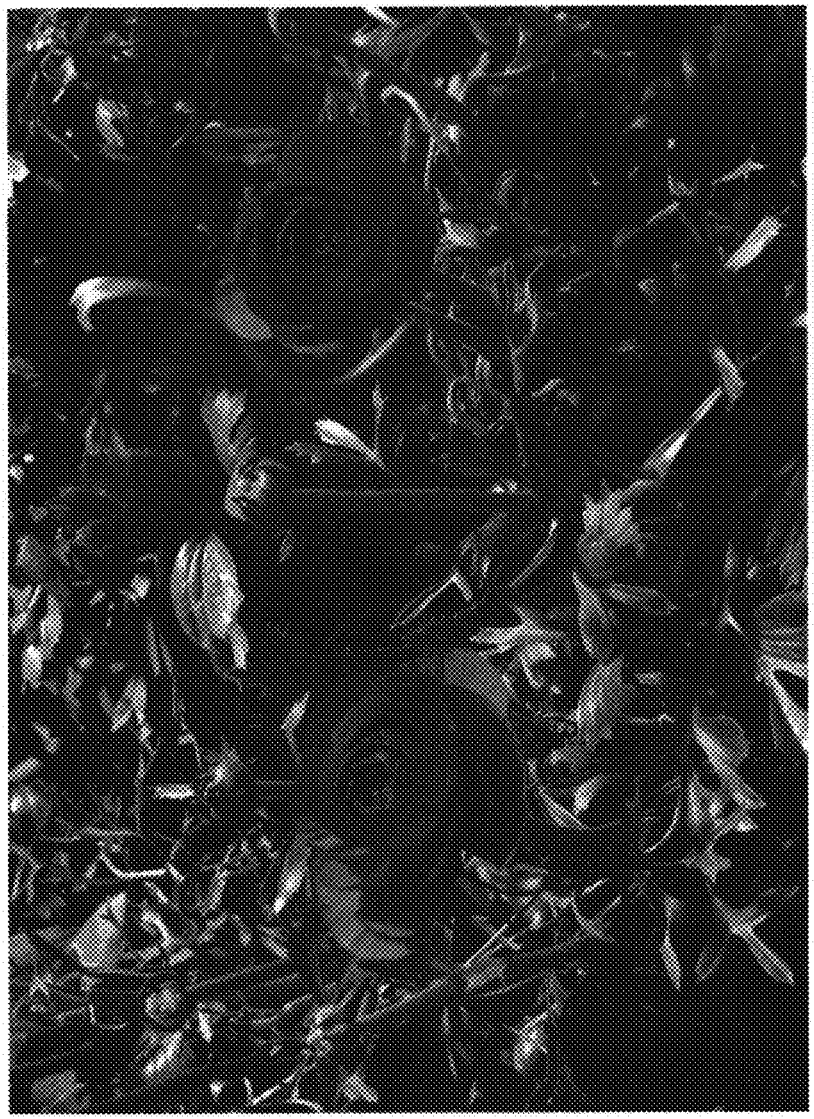

Latin name of the genus and species: *Ranunculus asiaticus*.

Variety denomination: 'ABIZANAGI'.

BACKGROUND OF THE INVENTION

The new *Ranunculus* cultivar is a product of a planned breeding program conducted by the inventor, Alberto Biancheri in Camporosso Mare, Italy. The cross resulting in this new variety was made during 2008.

The seed parent is the, unpatented, proprietary variety referred to as *Ranunculus* 'V239.01/C'. The pollen parent is the unpatented, proprietary variety referred to as *Ranunculus* 'P.sn2008/1'. The new variety was discovered in 2012 by the inventor in a group of seedlings resulting from the 2008 crossing, in a research greenhouse in Camporosso Mare, Italy.

Asexual reproduction of the new cultivar was first performed by vegetative division of buds sprouting from the rhizome of the selected plant. Subsequent propagation has been performed by tissue culture. First propagation took place at a research greenhouse in Camporosso Mare, Italy in 2012 and has shown that the unique features of this cultivar are stable and reproduced true to type in multiple successive generations.

SUMMARY OF THE INVENTION

The cultivar 'ABIZANAGI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ABIZANAGI' These characteristics in combination distinguish 'ABIZANAGI' as a new and distinct *Ranunculus* cultivar:

1. Bright magenta flower color.
2. Corolla size is large throughout flowering season.
3. Flower stems are generally above average in length.
4. Plants are highly productive and consistently produce quality flowers throughout the season.

PARENT COMPARISON

Plants of the new cultivar 'ABIZANAGI' are similar to plants of the seed parent, in most horticultural characteristics, however, plants of the new cultivar 'ABIZANAGI' differ in the following;

1. Flower color of the new variety is brighter than the seed parent. The main flower color of the new variety is Red-Purple 71A, the seed parent is near 70A.
2. Flower size of the new variety is larger. The new variety produces a larger flower, with an average diameter range of 10 to 13 cm, the seed parent has an average diameter range of 8 to 10 cm.

Plants of the new cultivar 'ABIZANAGI' are similar to plants of the pollen parent, in most horticultural characteristics, however, plants of the new cultivar 'ABIZANAGI' differ in the following;

1. Flower color. The main flower color of the new variety is Red-Purple 71A, the pollen parent is near 62B.
2. Flower size. The new variety produces a larger flower, with an average diameter range of 10 to 13 cm, the pollen parent has an average diameter range of 8 to 10 cm.

COMMERCIAL COMPARISON

Plants of the new cultivar 'ABIZANAGI' are comparable to the unpatented commercial variety *Ranunculus* 'ABIO- SHEKA'. The two *Ranunculus* varieties are similar in most horticultural characteristics; however, the new variety 'ABIZANAGI' differs in the following:

1. Vegetative carriage and plant size.
2. Floral stem of the new variety is longer.

BRIEF DESCRIPTION OF THE PHOTOGRAPHS

The accompanying photograph in FIG. 1 illustrates in full color flowering plants of the new variety at approximately five months old, grown in a greenhouse.

Figure 2:
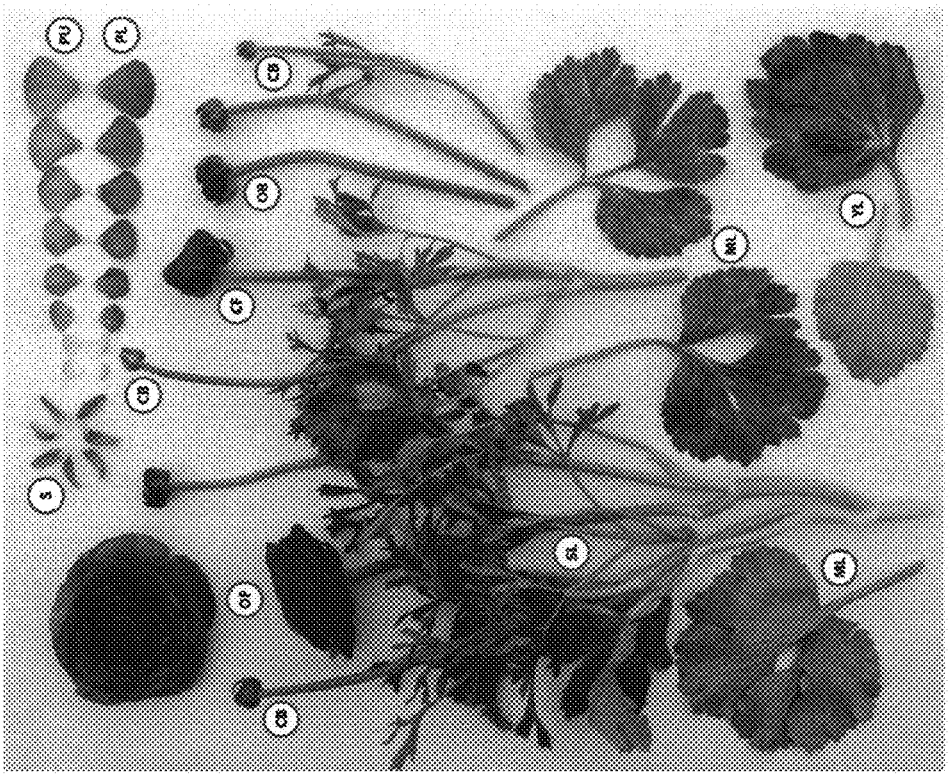

FIG. 2 illustrates a close up of plant parts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 6$^{th}$ edition, except where general terms of ordinary dictionary significance are used. The following observations and measurements describe 'ABIZANAGI' plants grown in a greenhouse Camporosso Mare, Italy. The plant described has been cultivated under glass, planted in the months of September and described in the month of February. One must always refer to these conditions of season and culture, when considering the present description. By reason of different climate or culture conditions, differences may arise between certain characteristics of the plant and the corresponding characteristics of the description. It should be considered as normal and do not modify the essence of the present invention because it will possible to identify the plant by means of the totality of the characteristics given in the description. The rhizome has been planted on raised benches in a peat and pumice substrate mixture. The growing temperature ranged from 12° C. to 25° C. during the day and from 2° C. to 8° C. during the night. General light conditions are bright, normal sunlight. Measurements and numerical values represent averages of typical plant types.

Botanical classification: *Ranunculus asiaticus* 'ABIZANAGI'.

Propagation:

*Time to rooting.*—15 days at approximately 10-12° C.

*Time to produce a rooted plantlet.*—20 days.

*Root description.*—Secondary roots grow from the rhizome and are fasciculate type.

Plant:

*Growth habit.*—Herbaceous perennial, robust plant, semi-prostrate vegetation.

*Height to top flower.*—60 to 70 cm.

*Plant spread.*—60 to 65 cm.

*Growth rate.*—Medium.

*Branching characteristics.*—Main floral stems grow from a basal rosette with 1 or 2 lateral branches, each one of which has a flower.

*Length of lateral branches.*—60 to 70 cm.

*Diameter of lateral branches.*—0.9 to 1.1 cm.

*Texture of lateral branches.*—Slightly tomentose.

*Internode length.*—Internodes are extremely close together, forming a basal rosette.

*Strength of lateral branches.*—Medium to Strong.

*Color of lateral branches.*—Yellow Green (RHS 144A).

*Aspect/angle of branches.*—20° to 30°.

*Number of leaves per lateral branch.*—Usually 2.

Foliage:

*Leaf.*—The leaves, usually numerous, have a marked heterophyllia, in relation to the degree of their development and their position on the plant (base of the plant; floral stem).

*Leaf at the base of the plant.*—Arrangement: Simple (young leaf, YL); Biternate (mature leaf, ML). Average Length: 30 to 40 cm. Average Width: 15 to 25 cm. Overall Shape of blade: Obovate (young leaf); Palmatipartite (mature leaf). Dissected leaves, describe lobes, quantity of dissection: Young leaves are generally not lobed; mature leaves are generally divided in 3 parts, each one of which further is divided in 3 lobes. Apex: Acute. Base: Rounded. Attachment: Base of the plant. Margin: Dentate. Texture of top surface: Slightly tomentose, slightly verrucose. Texture of bottom surface: Slightly tomentose, slightly rugose. Appearance of top surface: Matte. Appearance bottom surface: Matte. Leaf internode length: The internodes are extremely close together, forming a basal rosette. Color: Young foliage upper side: Green (RHS 137C). Young foliage under side: Yellow Green (RHS 147C). Mature foliage upper side: Green (RHS 137C). Mature foliage under side: Yellow Green (RHS 147C). Venation: Type: Dichotomous; plunging in to the limb at the upper surface; raised on the limb at the lower surface. Venation color upper side: Yellow Green (RHS 144A). Venation color under side: Yellow Green (RHS 144A). Petiole: Petiole: Long, tubular, rigid. Length: 20 to 24 cm. Diameter: 0.5 to 1.1 cm. Pubescence: Slightly tomentose. Color: Yellow Green (RHS 144A).

*Leaf inserted at the nodes of the floral stems (sl).*—Arrangement: Biternate. Average Length: 15 to 25 cm. Average Width: 15 to 20 cm. Overall Shape of blade: Palmatipartite. Dissected leaves, describe lobes, quantity of dissection: Generally divided in 3 parts, each one of which further divided in many deeply incised lobes. Apex: Acute. Base: Acute. Attachment: Floral stems. Margin: Dentate. Texture of top surface: Slightly tomentose. Texture of bottom surface: Slightly tomentose. Appearance of top surface: Glossy. Appearance bottom surface: Glossy. Leaf internode length: 10 to 20 cm. Color: foliage upper side: Green (RHS 137A). foliage under side: Green (RHS 138B). Venation: Type: Dichotomous, plunging in to the limb at the upper surface and raised on the limb at the lower surface. Venation color upper side: Yellow Green (RHS 144A). Venation color under side: Yellow Green (RHS 144A). Petiole: Petiole: Long, slightly flat, rigid. Length: 5 to 10 cm. Diameter: 0.7 to 0.9 cm. Pubescence: Slightly tomentose. Color: Yellow Green (RHS 144A).

Flower:

*Bloom period.*—Winter to Spring.

*Vase life (cut flower).*—10 to 15 days.

*Persistent or self-cleaning.*—Self-Cleaning.

*Bud.*—Closed bud (CB): Shape: Flattened globular with a sharp point. Length: 1.4 to 1.9 cm. Diameter: 1.3 to 1.5 cm. Color: Green (RHS NN137A); Purple Red (RHS 61A) along venations and near the base. Slightly open bud (OB): Shape: Flattened globular;

generally, the gynoecium is raised, clearly visible at the center of the corolla. Length: 1.5 to 1.9 cm. Diameter: 2.3 to 2.5 cm. Color: Purple (RHS N79B).

*Flower size* (*of*).—Diameter: 10 to 13 cm. Height: 2.8 to 3.5 cm.

*Corolla* (*of*).—Round, regular, in the form of a flat section.

*Petals.*—Arrangement: Imbricated, disposed on the receptacle in very tight verticils. The size of the petals is quite variable, according to the position in the corolla, decreasing from the exterior toward the center. The average size of fully developed petal is as follows: Lobe Length: 3.8 to 4.8 cm. Lobe Width: 4.6 to 5.6 cm. Quantity: Double flower, petals are very numerous (>100). Texture: Silky, thin, resistant. Lobe Apex: Rounded. Lobe shape: Obovate. Margin: Slightly Crenate. Aspect: Fan Shape, concave. Color when opening (CF): Upper surface: Red Purple (RHS N79C). Lower surface: Red Purple (RHS N79C). Color Fully opened (OF): Upper surface (PU): Purple (RHS 71A). Lower surface (PL): Purple (RHS 71A).

*Calyx to sepals* (*s*).—Quantity per flower: 6 to 9. Shape: Concave, moderately incurved. Length: 2.3 to 4.3 cm. Width: 0.8 to 1.1 cm. Apex: Acute. Base: Flat to Slightly rounded. Margin: Entire. Texture: Lower surface is tomentose; Upper surface is glabrous. Color Upper Surface: Green (RHS NN137 A) and Purple (RHS N79A). Color Lower Surface: Green (RHS NN137 A); Purple (RHS N79A) along venations and near the base.

*Peduncle.*—None.

*Pedicel.*—Length: 55.0 to 65.0 cm. Diameter: 1.3 to 2.0 cm. Color: Yellow Green (RHS 144A). Orientation: Upright, straight, rigid. Pubescence: Slightly tomentose.

*Fragrance.*—None.

Reproductive organs:

*Androecium.*—Stamens: Almost completely transformed as petals.

*Gynoecium.*—The pistils are numerous, short, locked together at the center of the corolla in a Yellow Green (RHS 144B) and Purple (RHS N79A), large, flattened, dome-shaped apocarpous gynoecium.

Other characteristics:

*Seeds and fruits.*—Seeds and fruit production not observed.

*Disease to pest resistance.*—Neither resistance nor susceptibility to normal diseases and pests of *Ranunculus* has been observed.

*Temperature tolerance.*—Upper and lower temperature tolerance not observed, plants have been grown in a climate controlled greenhouse. *Ranunculus asiaticus* typically tolerates temperatures within USDA Zones 7 to 11.

What is claimed is:

1. A new and distinct cultivar of *Ranunculus* plant named 'ABIZANAGI' as herein illustrated and described.

* * * * *